United States Patent
Austria et al.

(10) Patent No.: US 8,156,653 B2
(45) Date of Patent: Apr. 17, 2012

(54) SAFETY SCALPEL WITH BLADE RETENTION

(76) Inventors: Georgene Austria, Woodland Hills, CA (US); Pengcheng Ye, Ningbo (CN); Shenglei Di, Ningbo (CN)

(*) Notice: Subject to any disclaimer, the term of this patent is extended or adjusted under 35 U.S.C. 154(b) by 896 days.

(21) Appl. No.: 12/180,527

(22) Filed: Jul. 26, 2008

(65) Prior Publication Data
US 2010/0023039 A1    Jan. 28, 2010

(51) Int. Cl.
| B26B 3/06 | (2006.01) |
| F41B 13/02 | (2006.01) |
| F41C 27/18 | (2006.01) |
| A61B 17/00 | (2006.01) |
| A61B 17/24 | (2006.01) |
| A61F 11/00 | (2006.01) |
| A61F 9/00 | (2006.01) |

(52) U.S. Cl. ............ 30/162; 30/161; 606/79; 606/167
(58) Field of Classification Search ............ 30/161–162; 606/79, 83–86, 167–168, 170, 172
See application file for complete search history.

(56) References Cited

U.S. PATENT DOCUMENTS

| 5,071,426 A | 12/1991 | Dolgin et al. |
| 5,207,696 A | 5/1993 | Matwijcow |
| 5,275,606 A * | 1/1994 | Abidin et al. ............. 606/167 |
| 5,299,357 A | 4/1994 | Wonderly et al. |
| 5,330,492 A | 7/1994 | Haugen |
| 5,417,704 A | 5/1995 | Wonderly |
| 5,571,127 A | 11/1996 | DeCampli |
| 5,662,669 A * | 9/1997 | Abidin et al. ............. 606/167 |
| 5,741,289 A | 4/1998 | Jolly et al. |
| 5,938,676 A * | 8/1999 | Cohn et al. .............. 606/167 |
| 5,941,892 A * | 8/1999 | Cohn et al. .............. 606/167 |
| 6,254,621 B1 * | 7/2001 | Shackelford et al. ..... 606/167 |
| 6,589,258 B2 * | 7/2003 | Pilo et al. ................ 606/167 |
| 6,626,925 B2 | 9/2003 | Newman et al. |
| 6,629,985 B1 * | 10/2003 | Kiehne .................... 606/167 |
| 7,172,611 B2 * | 2/2007 | Harding et al. .......... 606/167 |
| 7,207,999 B2 * | 4/2007 | Griffin et al. ............ 606/167 |
| 7,346,989 B2 | 3/2008 | Shi |
| 2004/0243161 A1 | 12/2004 | Kanodia et al. |
| 2005/0065541 A1 * | 3/2005 | Abidin et al. ............. 606/167 |
| 2006/0100650 A1 | 5/2006 | Kiehne |
| 2006/0212058 A1 * | 9/2006 | Djordjevic et al. ....... 606/167 |

* cited by examiner

*Primary Examiner* — Ghassem Alie
*Assistant Examiner* — Bharat C Patel
(74) *Attorney, Agent, or Firm* — Law Office of Ken Dallara; Ken Dallara (57) ABSTRACT

A surgical scalpel is presented which combines the attributes of cost-effectiveness in design and safety of single use scalpel devices and the ability to be autoclavable so as to promote the device as a multiple use device as well. The design of the device is such as to afford medical personnel the feel, weight and balance of the original metal unguarded scalpel, while maintaining safety through the shielding of the blade during non-use and the ability to dispose of the blade in a safe controlled manner. The user is able to remove the blade through the biasing action of a living hinge and have it securely attached to the shield of the device for later discharge into a sharps container, all without having to place ones hands near the unguarded sharp. The device to designed to use existing styles of blades without needing costly inventories of specially created blades.

14 Claims, 7 Drawing Sheets

SAFETY SCALPEL WITH BLADE RETENTION

FIELD OF INVENTION

This invention covers the field of application where users are needing protection from accidental punctures from scalpel blades during the use and storage of surgical scalpel. More importantly, it is the capture and removal of the scalpel blades that is highlighted by this invention.

BACKGROUND OF INVENTION

Each year many users accidentally slice or puncture themselves with sharp instruments either during use, during transfer from one person to another or from inadvertent misplacement of sharps in potentially dangerous locations. This is especially dangerous in the medical arena, as potentially fatal diseases can be spread through accidental contact with sharps. Emergency Rooms are battlegrounds compared to the operating rooms where quick action amongst many people are required to save lives. Sharp protection is a must and must be easy to operate. Prior art is replete with many different style of devices that act to cover sharp blades.

There are 4 main types of prior art that exists to prevent users from accidental contact with sharp blades. The 4 areas involve devices where 1) the sharp is retracted into the body of the device, 2) where the device is a disposable or single use application, where the entire sharp with the handle is not reused, 3) a device that moves in a non-linear fashion to cover the blade while it is not in use, and 4) those devices which remove a detachable blade from the handle of the device.

In the first arena of prior art, patents have been granted for devices mainly in the medical field. The basic premise for this group of patents is that the blade is extended from and retracted back into, the handle of the device. There is usually one handed operation of these devices, but the Shapiro U.S. Pat. No. 5,571,128 issued on Nov. 5, 1996 discloses a device that requires "rotary and longitudinal movement of the handle" to move the surgical element. That extra step of motion can be difficult if the surgeons hands are busy holding or manipulating another device. Most patents use devices that are similar in shape to existing scalpels but are machined or molded in such a manner to create a hollow in the body of the scalpel to hold serve as a chamber to store the blade while not in use. The Dillion et al U.S. Pat. No. 5,730,751 and the Cote et al U.S. Pat. No. 5,431,672detail this style of retracting blade into the body prior art. Dillion provides for "an inoperative location within the handle" and Cote states that the blade is slid from an "intermediate position where the blade is within the handle". Both Cote and Dillion provide for the location of the triggering mechanism to retract the blade is nearest the distal or blade end of the device. Cote discloses the triggering mechanism on the side of the handle which could disturb the surgeon as that is the natural position of the surgeons hand during use and possibly hinder the operation of the scalpel should it be used in a tight surgical location such as under the arm or in persons with layers of fat, where the scalpel is often used past the coetaneous layers of the body. Both Cote and Dillion function only with their respective blades and handles are not transferable to current scalpels in use. There are also issues present that would make the sterilization after use of these devices to be difficult if possible at all. U.S. Pat. No. 5,662,669 issued to Abidin et al on Sep. 2, 1997 discloses a highly complex internally retractable scalpel. As with most internally retractable scalpels they would constitute single use as they are not autoclavable. With the complexity of the internal parts and springs, there are not adequate steam paths for cleaning. This makes for a very expensive single use application.

The second arena of prior art involves the use of single use blades and handles. There are three main styles where the either the blade is retracted into the body, a shield is produced covering the blade or there is a separable device that is used to cover the blade. In the first style, Dambal et al in U.S. Pat. No. 6,757,977 issued on Jul. 6, 2004, Haining in U.S. Pat. No. 5,330,493 issued on Jul. 19, 1994 and U.S. Pat. No. 5,556,409 issued on Sep. 17, 1996, all disclose devices where the blade is first extended for a single use and then is withdrawn into the body and some mechanism will prevent the blade from being extended in the future. Thus making this device safe for disposal after a single use. While Dambal and Haining uses a manual method, thumb power, to retract the blade, Flumene et al in U.S. Pat. No. 6,022,364 issued on Feb. 8, 2000, is "operated through an elastic returns means". The second style involves the uses of a shield that moves over a stationery blade. Wonderley in U.S. Pat. No. 5,417,704 issued on May 23, 1995, discloses "a blade carried by the handle adjacent one end thereof and a guard movably mounted to the handle for sliding movement relative to the handle between a protective position covering the blade and a retracted position exposing the blade." Where Wonderley discloses a manual operation to move the shield into the desired position, Pilo et al in U.S. Pat. No. 6,589,258 issued on Jul. 8, 2003 discloses the use of an "elastic return elements to bring the blade back into the retracted inoperative position". U.S. Pat. No. 7,153,317 to Kanodia et al issued on Dec. 26, 2006 discloses a typical inexpensive single use device where a shield slides over the handle exposing the sharps device. There is a positive lock preventing and visual indicia showing that the scalpel is not be reused. The third style as disclosed by Williams in U.S. Pat. No. 4,735,202 issued on Apr. 5, 1988, uses a separable shield device on a round handled scalpel that is removed and remounted after use. All of styles mentioned in this section involve the use of unique surgical handles and blades which are disposed of after use. This is an expensive alternative as the majority of the cost of a normally used scalpel is in the high precision surgically ground blade. It is not economically justifiable to use this method when medical costs are escalating very rapidly. Also the major problem with the single use style of scalpel is the lack of "feel" for surgeons. Metal handles have a balance and weight that the users are comfortable with and the single use style typically are much lighter and are tip-heavy versus handle heavy producing a different feel.

One issue with the aforementioned "single" use scalpels is the problem with reuse. U.S. Pat. No. 7,346,989 issued to Shi on Mar. 25, 2008 discloses (Col 1 Line 27) that scalpels available nowadays, however, can be reused due to the deficiency of the configuration. Shi claims a "deadlock" recess that prevents the reusing of single use scalpel where the removal of the blade is not an option. This is an added cost that reduces the cost efficiencies of using single use blades in the first place.

The third arena of sharps protection involve the use of a guard that moves to cover the sharp but does so in a non-linear path or motion. Landis et al in U.S. Pat. No. 5,843,107 issued on Dec. 1, 1998 and Schneider in U.S. Pat. No. 5,250,064 issued on Oct. 5, 1993 disclose a shield that is actuated by the surgeon's thumb, whereby a protective member is lifted away from the sharp during use. This presents several issues; as the surgeon's thumb is not naturally located above the blade during or prior to use, the cover would present sight issues as it would be in the line of sight of the surgeon during use, the cover would prohibit the use of the blade subcutaneously as is required in certain surgical procedures or involving persons who are overweight and it requires that the surgeon pay attention to something other than the patient as the surgeon must be aware of holding the shield in position. Though both of these patents allow for use on existing sharps, it involves the placement of the devices next to the sharp where there exist a large chance of accidental puncture. Capewell in U.S. Pat. No. 5,478,346 issued on Dec. 26, 1995 also discloses a sharps guard but here there is "a blade guard attached to the scalpel by a frangible tether". Capewell uses a non-standard scalpel for this application and requires the user to move their fingers next to the sharp to operate this guard. This guard also contains the problems associated with the Landis and Schneider patents as well.

The fourth arena of the prior art involves the use of devices whereby the sharp is attached to and then removed from the handle. In one group, there are those devices where the sharp is directly attached to the handle and another group contains devices where the sharp is placed into a cartridge which is then placed upon the handle. Both groups involve handling of the sharp prior to it's inclusion into some protective cover, increasing the chance of accidental puncture. In the first group, Herbert et al in U.S. Pat. No. 5,868,771 issued on Feb. 9, 1999, Newman et al in U.S. Pat. No. 6,626,925 issued on Sep. 30, 2003 and van der Westhuizen et al in U.S. Pat. No. 5,330,494 disclose the procedure of attaching the sharp to the handle and then attaching a sliding blade guard. Once the sharp is used, the blade can be removed along with the guard. Herbert uses existing style surgical handles, while van der Westhuizen and Newman use a unique handle that is modified at the distal end of the handle nearest the sharp, to receive the guard. Both devices require the user to load the sharps device onto the handle, requiring the unguarded sharp to be handled by those that the device is designed to protect, and often those people are wearing gloves which will reduce tactile feel. In a different approach disclosed by Noack in U.S. Pat. No. 5,312, 429 issued on May 17, 1994, where a unique blade with an opposed tang is removed by sliding blade release element when the element is slid down the handle toward the sharp. This is a two handed operation involving two separate pieces. In the sliding of the element, if one's hand slips from the element it would be certainly by cut by the exposed blade. Also the blade is without direction or restraint when released from it's location on the handle. It could fly anywhere in the operating room as there is tension built up between the tang of the blade and the rest of the blade that was forced over the post on the handle.

Cartridge types highlighted by U.S. Pat. No. 7,207,999 to Griffin et al issued on Apr. 24, 2007, show the use of a cartridge that contains the blade for the scalpel. The cartridge doubles as a shield when it is retracted over the handle after the attachment of the blade to the tang of the handle. Each cartridge is unique to a particular style of blade and requires a two handed operation to remove and attach the blade. This extra cartridge material creates costly waste. It is also against current disposal regulations to mix plastics with metals sharps containers are they require different disposal techniques. U.S. Pat. No. 7,172,611 issued to Harding et al on Feb. 6, 2007 shows another cartridge but this one is required to use a special blade with "non-arcuate" holes which increase the cost and decreases it's effectiveness to be used with a broad range of access. All cartridge style scalpels use the removal of the cartridge that contains the blade as the means for blade removal. Though safe, these devices are limited by needing unique cartridges to hold the wide variety of blades available.

Another adaptation of this concept, which is closer to the current invention, is found the series of patents from Jolly et al, U.S. Pat. Nos. 5,827,309, 5,752,968 and 5,792,162 issued Oct. 27, 1998, May 19, 1998 and Aug. 11, 1998 respectively. These Jolly patents show a blade remover which first removes the tang of the blade from the post into a notch on the sliding guard. Then '968 discloses that "guard 30 can be advanced distally to force blade 50 from blade carrier". The built in stresses mentioned above are now increased with a forcible removal of the blade with the sliding guard, increasing the chance for the blade to misdirected about the operating room. In the second group, Gharibian in U.S. Pat. No. 5,527,329 issued on Jun. 18, 1996 and Cohn et al in U.S. Pat. No. 5,938,676 issued on Aug. 17, 1999 disclose the use of a cartridge system whereby the sharp is placed into a cartridge which is then encased by a guard prior to it's placement onto the handle. This operation is safer as the sharp is guarded during assembly but creates a situation as each discloses a unique handle designed to receive the cartridges and shields. Cohn et al in U.S. Pat. No. 5,941,892 issued on Aug. 24, 1999 combines prior art by incorporating the cartridge concept that is "removably retained within the cavity" in the handle. This is a safe alternative but uses unique handles. All of the prior art in this section requires the use of two hands to safely operate the device which is at odds with current FDA compliance rules.

In the last arena of prior art, a guard is placed around a stationery blade. There is nothing unique about the concept, and it's application can be seen from the simple to the complex. Applications of a more complex nature are found in Abidin et al in U.S. Pat. No. 5,662,669 issued on Sep. 2, 1997 and U.S. Pat. No. 5,569,281 issued on Oct. 29, 1996, Jolly et al in U.S. Pat. No. 5,741,289 issued on Apr. 21, 1998, Matwijcow in U.S. Pat. No. 5,207,696 and Dolgin et al in U.S. Pat. No. 5,071,426 issued on Dec. 10, 1991. Matwijcow discloses a rack and pinion system for movement of the guard over the blade which causes a reverse sequence of logic, as the user needs to pull back to move the guard forward. This could be confusing in the fast paced operating room where several different type of devices might be used at once. Dolgin also uses a "linkage system" to extend the blade guard "over a substantially greater distance than the distance which the surgeon's fingers move in operating the actuating mechanism". This is unnecessarily complex and expensive concept using unique handles which requires manual loading of the blades onto the handle. Jolly provides for both linear actuation of the guard along with a rotational movement of the guard and blade away from the handle for cleaning purposes. This device is complex and expensive to manufacture and use. The Abidin '281 patent discloses a guard which "comprises an inverted U-shaped channel member telescopically mounted within the hollow handle for sliding movement therein". It is held in position by exposed an exposed pin which would be in the way of the surgeon's hands and could be accidentally triggered to move at the improper time. This device is also not usable with currently used scalpels and it requires a unique handle. Abidin '669 is another internally guided blade guard with a unique handle. But this patent also discloses in column 10 line 11, that it does not work with conventional scalpel blades. '669 does combine a blade guard and a blade ejector, but FIG. 36 details the need for two handed operation to remove the blade. FIG. 45 and FIG. 48 show that the blade is not restrained after it is removed from the handle, and as described above, there is a considerable amount of tension on the blade. The disclosure details the added tension as the guard actually pushes the blade off of the post upon which it is attached. There is nothing to restrain the loose blade. An unrestrained blade could fly off anywhere in the operating room and this is not a safe method of removal. '669 also discloses in FIG. 32 the complicated way of attaching the blade with two small pins, which would be very difficult with gloved hands in a hurried operating room. FIG. 13D of '669 shows the user sliding the guard forward using their forefinger, which would present an obvious problem, should the guard become slippery due to bodily fluids, and the user's finger slips from the guard onto the exposed blade.

There is a need to preclude the problems associated with the prior art and the current state of technology in this field. It would be preferable to produce a device that would provide current users with a device that would improve upon some of the shortcomings of the prior art. Industry has set standards for their equipment and it would be desirable to have a device that fits their standard equipment, rather than adapt to new equipment. Sharps users, especially surgeons, are used to the weight, balance, fit, form and feel of their tools of the trade, and are reticent to change. It is well practiced in the medical field, that metal sharps handles are used because they possess a certain weight and balance that plastic handles have a hard time replicating. Industry needs to adapt protections to currently used sharps, as new device are usually meet with skepticism and doubt, and are thus not used. Industry does not want to carry duplicative inventories of many similar products because they do not work with one another.

It would be desirable to have a new device be made in such a manner that it would be reusable and manufacturable in great quantities, lower product costs while assuring repetitive quality throughout the devices could even make this product disposable after a single use. It would be desirable to have the device made of autoclavable plastic or metal and designed so that it will not have any hidden recesses or other cavities that would trap harmful bacteria precluding the chance that it could be autoclavable. It would be desirable and advantageous to possess a blade removing apparatus which is designed where the blade is held rather than just pushed off the blade post creating a more secure environment.

It would be desirable to have a scalpel to be able to be able to easily remove and change blades during surgical procedures, whereby one handle is capable receiving multiple sizes and shapes of blades

BRIEF SUMMARY OF THE INVENTION

Accordingly, it is the goal of this invention to create a sharps protection device that has the aforementioned characteristics of simplicity, protection, adaptability to current uses and safety. It is an object of this invention to create a device that will protect both the user of the sharp as well as the person who comes in accidental contact with misplaced sharps, and for the person to whom the sharp is transferred. It is also an object of this invention to create a device which can be autoclavable should the user desire such reusability yet be cost-effectively designed to minimize cost to make single-use an economic reality.

Accordingly, it is the goal of this invention to create a sharps protection device that has the aforementioned characteristics of simplicity, protection, adaptability to current uses and safety for use with scalpels. It is an object of this invention to create a device that will protect both the user of the sharp as well as the person who comes in accidental contact with misplaced scalpels, and for the person to whom scalpel is transferred.

It is an object of this invention to create a device that is operable with a single hand and allows for the user to be either left or right handed to operate the device. The user must be able to retract or extend the sharps guard and be able to remove the sharp from the handle if that option is available to the user with the particular sharp.

It is an object of this invention to create a device that does not interfere with the normal operation of the scalpel and that it does not substantially change the feel of the scalpel. It is an object of this invention to create a device whose design allows for the modification of said design altering the weight and balance characteristics while maintaining overall design allowing for interchangeability.

It is an object of this invention to create a device that is rapidly interchangeable between a wide range of sharp's blades. The device must be simple to use and maintain. Users must be able to disassemble, clean, and reassemble in a matter of moments, while using gloved hands with reduced tactile feel. The device must have no small or intricate parts which would preclude the quick assembly of the device.

It is an object of this invention to create a device which adapts in fell, balance and weight to current state of the art devices, reducing the need for training, evaluating and maintaining multiple inventories of devices and sharps. It is an object of this invention that industry standard blades, which are accepted onto a wide range of currently existing handles, are to be used without modification to the blade or handle.

It is an object of this invention to create a device which has positive stops, including tactual and auditory signals, indicating the relative position of the guard, either in retraction or extension of the surgical safety scalpel with blade retention.

It is an object of this invention to create a device that does not involve placing of the protective device over the sharp in such a manner that actually increases the likelihood of accidental contact with the sharp. The user should be able to use the device immediately "out of the box" without having to add guarding or assemble cartridges prior to safe use.

It is an object of this invention to create a device that will provide for safe removal of the sharp from the surgical safety scalpel with blade retention without the possibility unknown trajectories. It is a further object of this invention is to have the sharp blade covered during the time the users hands are ejecting the blade, thereby reducing the chance for accidental puncture It would be desirable to create a device which is sterilizable, and cleanable without disassembly, internal voids, sharp corners, chambers or holes which trap unsanitary material precluding the ability to easily clean and sanitize the device through autoclaving or reuse of the device.

DETAILED DESCRIPTION OF THE DRAWING FIGURES AND INVENTION

The following detailed description of the drawing is provided to show the enablement of the aforementioned principles in connection with this invention as it applies to the medical field, where surgeons, nurses and operating room personnel, as well as emergency medical technicians and paramedics in the field, need protection from accidental puncture or lacerations from unguarded scalpel blades.

The hereinafter described invention can be used as a single use scalpel or as a multiple use scalpel. It is an object of this invention to provide the user with this option and the components are designed with the ability to be multi-use. This multi-use capability is developed through the use of steam channels, lack of hidden or reverse recesses and materials are that able to be sterilized in an autoclave. The materials used to construct this device can be metal or an autoclavable plastic such as the blend of polyphenylene oxide (PPO) and polystyrene developed by General Electric sold under the trade name— Noryl. Single use versions can be made of a variety of plastics such as acrylonitrile butadiene styrene (ABS) or Nylon, possibly containing a filler based on the weight of the device desired.

Figure 1:
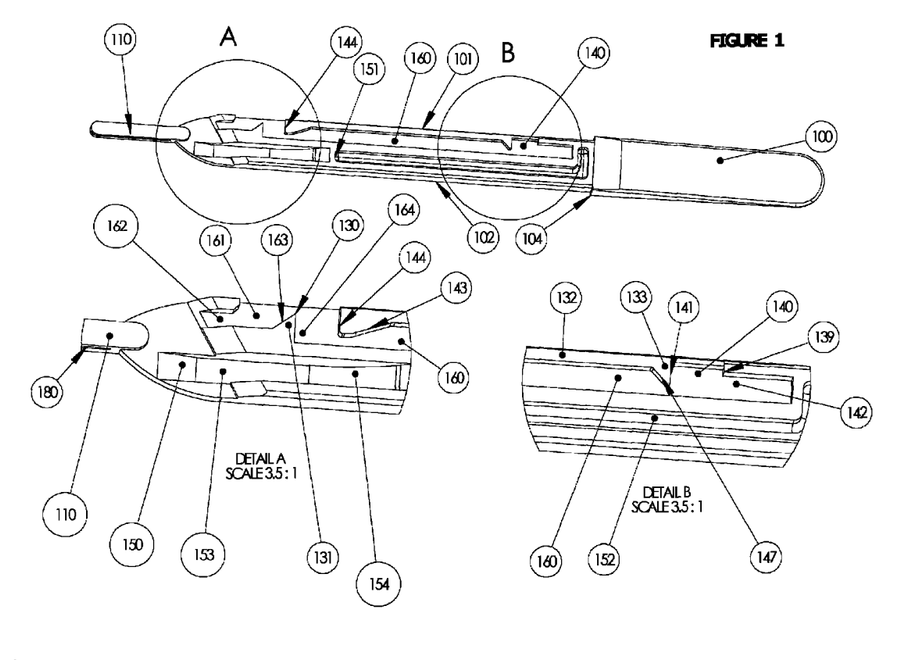
FIG. 1 is a detail side elevation of the scalpel handle
Figure 6:
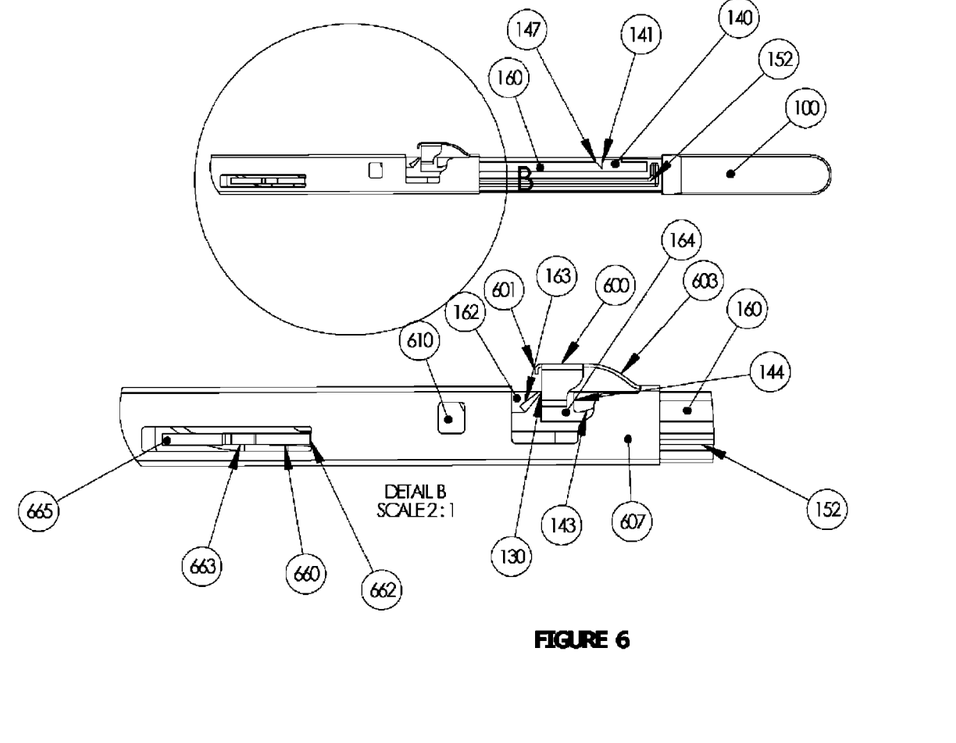
FIG. 6 Shows the combination of the shield and handle in the closed position.

FIG. 1 shows the left side elevation of the handle of the scalpel. Tang holder 110 is on the distal portion of handle 100, holder 110 containing tang slot 180. Immediately anterior to holder 110 along leading edge 101 is shield engagement locator 162 which leads into engagement slot 161. Engagement slot 602 on shield lock 600 shown on FIG. 2 slides past locator 162 in a semi-depressed state into slot 161 meeting an inclined escarpment or engagement slope 163 causing the lock 600 to extended above the rest position. After passing disengagement point 130, the lock 600 relaxes to it's rest position. This operation of attaching the shield can be done in the presence of a blade 111 as seen in FIG. 6. The shield is in the forward position covering the blade and is held in place as engagement slot 602 on shield lock 600 is held in place between the vertical faces of forward stop 131 and the distal vertical face 144 of travel rail 132. The shield locking mechanism controls the linear position of the shield. The lock is in it's natural state requiring positive displacement of lock 600 to move the shield distally or proximally. Travel slot 160 defines the scope of travel of the shield as it traverses along the longitudinal axis of the handle between the forward stop 131 and rear stop 133. Frame stop 104 provides a positive stop preventing any further rearward travel of the shield.

Figure 4:
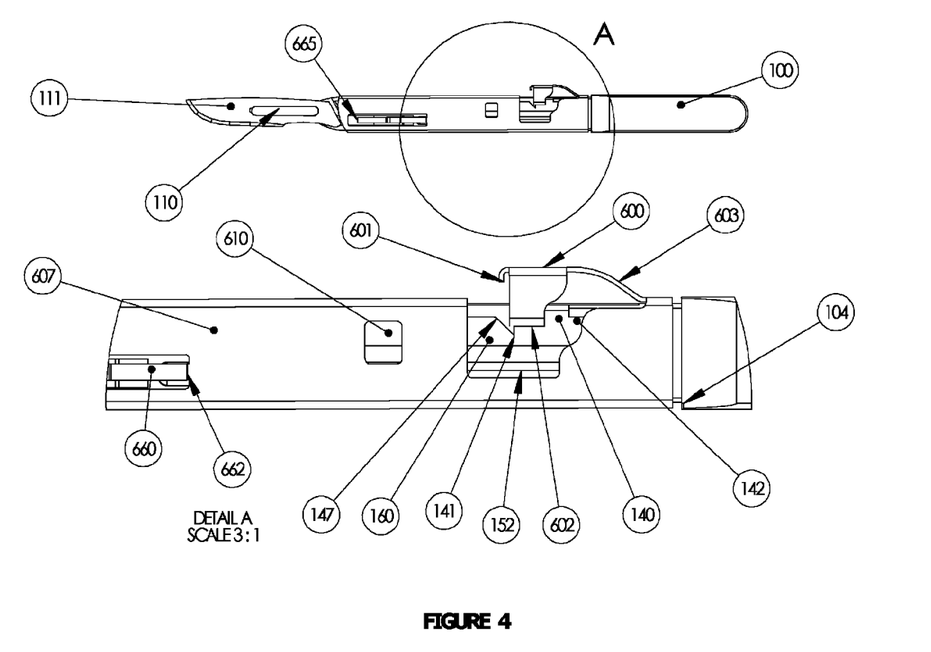
FIG. 4 is the combination of the shield on the handle in the rearmost or active position.

Upon depression of lock 600 by the user, motion rearwardly of the shield exposes the blade as the shield is guided by travel slot 160 until slot 602 contacts rear slope 147 of rear stop 133. This slope causes the natural compression of the lock 600 giving the user tactile feel of approaching the rear extend of the shield displacement and provides support to stop 133. Rearward slopes 147 and forward slope 143 provide tactile feel to the user that they are approaching a stop. Prior to that contact with the slopes, slot 602 has minimal contact with the rail 132 reducing friction. Further rearward progress guides the shield and slot 602 into the rear engagement area 140, which is shown in FIG. 4, which provides a positive lock of the shield in the rearward position. Slot 602 is securely held between the vertical face 141 of stop 133 and rear shelf 139. Travel slot 160 continues proximally into the upper steam slot 142 which allows for the transgression of steam along the longitudinal axis of the handle during the autoclaving procedure.

Figure 5:
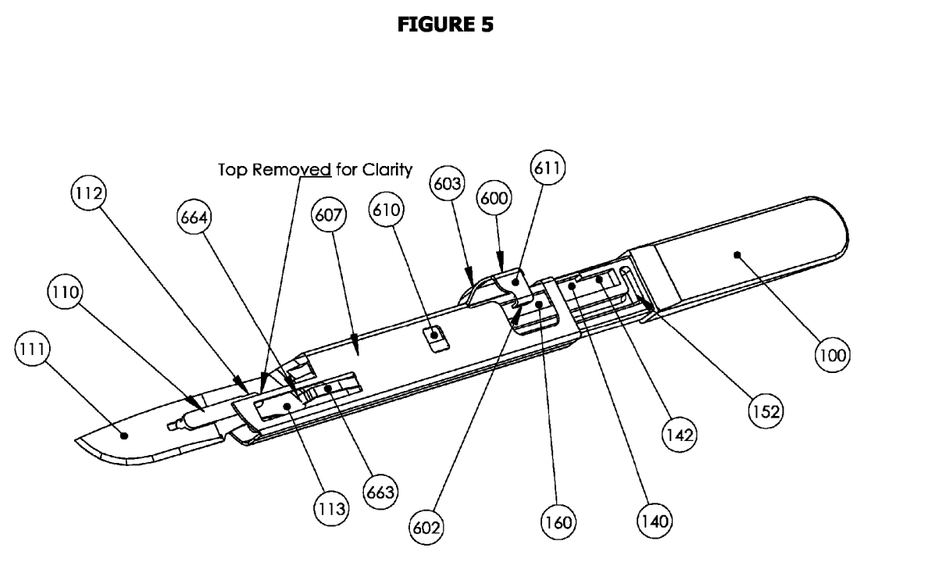
FIG. 5 shows the use of the blade disengagement mechanism removing the blade from the tang.

Immediately anterior to holder 110 along trailing edge 102 as shown in FIG. 1 is the ejector bay 153. Bay 153 is defined by an ingress slope 154 and ejector guide slope 150. Bay 153 serves as a guide for the ejector pin that can remove the tang 113 of blade 111 from rear of blade holder 112. While the user is pressing the surgical sharps ejector mechanism attached to the shield, the user is also providing forward motion towards the distal end of handle 100 and bay 153 provides the centering and guidance necessary to remove the tang. FIG. 5 shows the action of removing the blade from the tang holder which will be discussed later. Proximally located to Bay 153 is ejector wall 151 which separates the ejector bay 153 from lower steam slot 152. The shape, length and contour of steam slot 152 is dictated by the weight and balance desired by the user prior to manufacturing. Steam slot 152 has a vertical component at the proximal end of the handle whereby steam is allowed to exit. The slot removes excess material and thus cost, but also allows for steam to pass through during the autoclaving process while the shield is in place. It is an object of this invention to allow for sterilizing of the of the unit while it is together, preventing the need for extra operation and lost parts. Wall 151 serves as the tactile response to the user signifying that the ejector mechanism is in place to begin the removal process. Ejector 665 has a rectangular shape and slot 152 is designed to be narrower than the width of ejector 665 preventing the user from engaging the ejector mechanism prior to it's introduction into bay 152.

Figure 2:
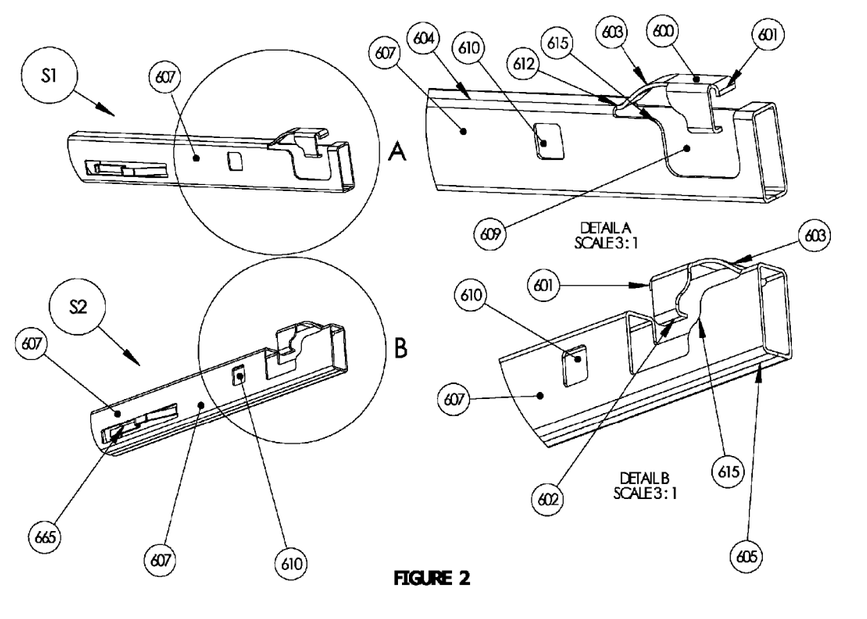
FIG. 2 details the shield that is used with the handle showing two different approaches to the attachment of the locking mechanism.
Figure 3:
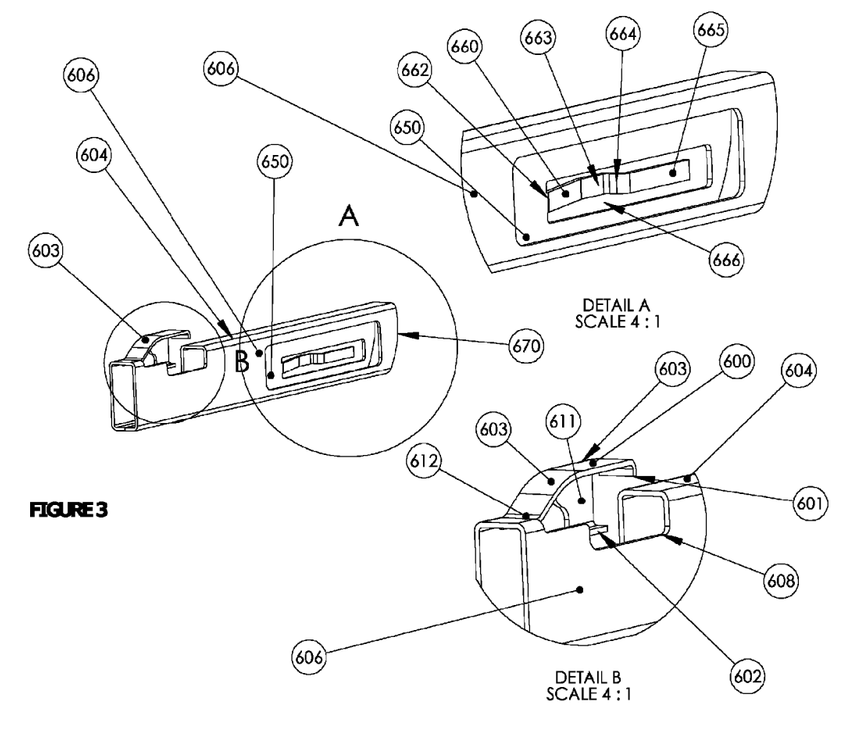
FIG. 3 is a detail of the blade disengagement mechanism common to both styles of shields.

FIGS. 2 and 3 detail the shields S1 and S2 that are basically similar in shape and function but have lock 600 facing in opposite fashions. Lock 600 is attached to the upper portion of the shield 604. Shield is defined as a 4 sided box shape with an exterior and matching interior sides, having an upper portion 604 and a lower portion 605 along with a left side 607 and a right side 606. The shape of the shield matches the rectangular shape of the handle and is closely dimensioned to that of the handle to allow for minimal interference between the shield and handle. The distal end 670 is curved and contains the ejector mechanism and access window shown on FIG. 3 and the proximal end containing the locking mechanism 600 and blade number window 610. Window 610 is arranged so that in the closed position the industry standard location of the number of the blade can be seen. This serves as a visual check to confirm the correctness of the blade prior to the opening of a sterile package only to find the incorrect blade marked on the outside of the package and also serves as an identifier during surgery, where it is possible to have several different scalpel blade sizes required during a single operation.

Locking mechanism 600 is attached to upper portion 604 using living hinge 612 to provide a pivot point through which mechanism operates, where height of the mechanism is controlled by length of adjustment 603 and the mechanism pivots through the contoured opening defined by contour edge 615 along the left side 607 of the shield. Shield S2 has a similar contour 608 along the right side 606 to relieve the shield of excess unneeded material, and that configuration is also available on shield S1. Forward latch 601 protects the forward edge of the mechanism and provides a ledge to provide traction when raising the mechanism upwardly when removing the shield from the handle in the forward position over forward stop 131. The larger ledge allows for the use with gloved fingers while operating. Engagement slot 602 is held in a position as to be parallel with the travel slot 160 at a distance from button 613 through the use of tab 611.

The distal end of the shield contains on one side the ejector mechanism and the other side either a viewing port 650 or a set of vertical baffles (not shown) which is the preference of the user. In FIG. 3, the ejector mechanism is shown on the left side to match the location of ejector bay 153 with which it interfaces. There is nothing limiting the ejector mechanism being on the left side so long as the ejector bay 153 matches it on the proper side. The ejector mechanism consists of living hinge 662, extender 660, ejector flat 663, angled tang contact 664 and ejector 665 all functioning through ejector window 666.

Figure 7:
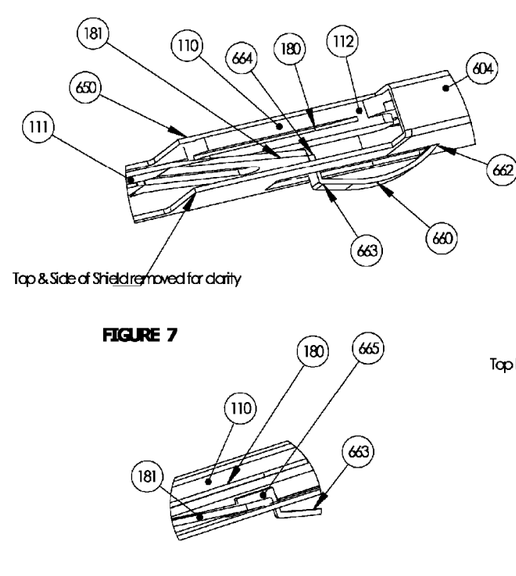
FIG. 7 is a detail of the blade being removed from the tang
Figure 8:
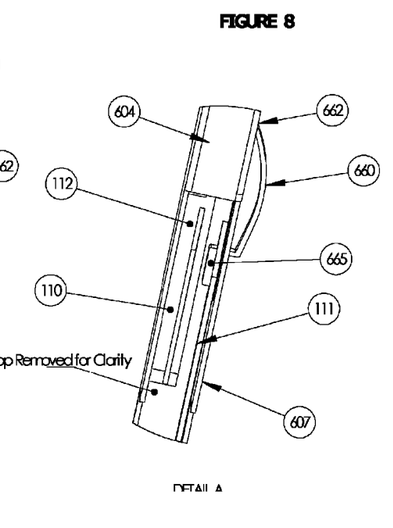
FIG. 8 shows the blade after removal from the tang as it is secure held in place against the side wall of the shield.

FIG. 5 shows the operation of removing the blade from the device. This device can be used as a single use scalpel where the user will place the shield in the closed position and discard of properly or the user can chose to remove the blade and place the unit in an autoclave for sterilization. The user with one hand, depressing the button 613, applies pressure moving the shield towards the closed position. The user bring the other hand and depresses ejector flat 663 until ejector is guided into the ejector bay 153, whereby the ejector 665 is directed into a position behind and opposite of blade tang 113. Additional movement of the shield toward the distal end of the handle will cause tang contact 664 to become flush with the tang 113. Due to the elastic or spring nature of the design of the ejector mechanism, the tang of blade 113 will be eased off of the rear of blade holder 112. FIG. 7 details the interface between the ejector 665, contact 664 and blade 111. Further motion towards the distal end of the handle will remove the blade completely from blade holder 110. It is the predictable self-biasing nature of the convex design of the ejector mechanism, where the living hinge's natural tendency to remain open due to the material stiffness properties of extender 660 and presence of material behind the living hinge 662, the has the tendency to pull the mechanism back to it's original position trapping the blade 111 in it's path. Blade 111 is now held securely to the inside wall of the shield due to the spring nature of the design of the ejector mechanism. FIG. 8 shows the blade held awaiting for the user to either again press the ejector flat 663 and guide the sharp into a proper disposal means or to remove the shield by reversing the assembly steps and disposing of both the shield and blade into a disposal means.

It is critical to observe that it is the design of the steam vents and lack of interior voids that allows the device to be autoclavable without the need to separate the shield from the handle. This design focuses on the need to reduce extra handling and reduce the possibility of accidental sharps punctures by not exposing the sharp unless the user specifically makes the effort to expose it. The device can be autoclaved in the open or closed position.

It is critical to observe that the ejector mechanism functions as a result of the natural resistance of the shield material to change in it's alignment, and that it is the high bending stiffness of the material that wants to return the ejector mechanism back to it's natural state that traps the blade against the shield. The design of living hinge 662 and extender 660 and the material chosen are key components of the ability to hold the blade against the shield. Spring steel, stamped stainless steel and plastics with a low modulus of elasticity, which increases stiffness and memory and also has a high resistance to thermal stresses, such as polystyrene blends, nylon or polypropylene can be used.

It can be appreciated by those appropriately skilled in the art that changes, modifications or embodiments can be made to this invention without departing from the spirit, principles, theories, ideas or conceptions that have been disclosed in the foregoing. It is herein recognized that the embodiments disclosed by this description of the best mode of practicing this invention, which will be hereafter described in their full breadth in the claims and equivalents thereof.

What is claimed is:

1. A surgical scalpel assembly comprising;
a single piece handle, having two vertical sides and two horizontal sides which terminates said vertical sides, whereon a surgical scalpel sharps blade is capable of secure attachment at the distal end of said handle, said handle designed to have an upper longitudinal travel channel and a lower separate longitudinal steam slot to allow for passage of sterilizing autoclave steam, said travel channel and said steam slot located along the same vertical face of said handle, said handle having a lack of non-autoclavable interior voids, and having an ejector bay longitudinally position along one of said vertical sides at said distal end of said handle, and
a shield, said shield having four sides whose vertices form a rectangular cross-sectional configuration having an interior and exterior portion and opposing vertical and horizontal surfaces, capable of circumferentially interfacing with said handle, having a distal end and a proximal end, containing a surgical sharps ejection mechanism located distally along said vertical surface where said surgical sharps ejection mechanism is deflected laterally by application of a load element, said sharps ejector mechanism possessing a self-biasing action to return said ejector mechanism to a natural convex shape through natural intrinsic exertion of maximum resistive forces to said resultant deflection, a shield locking mechanism interfacing with said longitudinal travel channel of said handle, and a blade number recognition means, said shield capable of linear transitory motion between fully covering said attached surgical sharps blade in a closed position and fully uncovering said attached surgical sharps blade in an open position, said shield capable of assembly and disassembly from said handle.

2. A surgical scalpel assembly as in claim 1 where said steam slot is designed to allow for said handle and said shield to be autoclaved whilst said shield is located thereupon said handle in either said open or said closed position.

3. A surgical scalpel assembly as in claim 1 where said shield is capable of linear movement between said open and said closed position with using a single hand and where the locking button of said linear positioning control mechanism is distally located away from user's fingers during use of said scalpel.

4. A surgical scalpel assembly as in claim 1 where said shield locking mechanism interfaces with said longitudinal travel channel of said handle, said shield locking mechanism interface being an engagement slot perpendicular to said longitudinal travel channel.

5. A surgical scalpel assembly as in claim 1 where said longitudinal travel channel contains a rearward open shield securement area with tactile and auditory response to proper location requiring positive displacement when shield is rearwardly located and said blade is exposed.

6. A surgical scalpel assembly as in claim 1 where said longitudinal travel channel contains a forward closed shield securement area with tactile and auditory response to proper location requiring positive displacement when shield is forwardly located and said blade is covered.

7. A surgical scalpel assembly as in claim 1 where said shield locking mechanism has minimal frictional contact with said guide passageway during longitudinal linear movement.

8. A surgical scalpel assembly as in claim 1 where said longitudinal travel channel contains inclined tactile feel escarpments prior to engagement of said shield locking mechanism into said shield securement areas.

9. A surgical scalpel assembly as in claim 1 where said steam slot is volumetrically shaped to maintain the balance and weight of industry standard scalpels.

10. A surgical scalpel assembly as in claim 9 where said blade ejector mechanism is shaped to go behind said sharps blade, along said ejector bay of said handle, said mechanism laterally removing the tang of said blade from said distal end of said handle, said mechanism solely using said self-biasing action of said ejector mechanism to remove said blade.

11. A surgical scalpel assembly as in claim 10 where said removed sharps blade is positioned against interior portion of said shield and is prevented from displacement due to said self-biasing action of said blade ejector mechanism, said positioned sharps blade being released by subjecting said ejector mechanism to a load.

12. A surgical scalpel assembly as in claim 10 where said removed blade is positioned against interior portion of said shield and is prevented from displacement due to said self-biasing action of said ejector mechanism, said shield and said positioned blade being able to be disposed of by removing said shield from said handle by raising said slot of said positioning control mechanism and disposing of said blade and said shield into a sharps containment disposal means.

13. A surgical scalpel assembly as in claim 9 where said steam slot is shaped as to not allow for entry of said blade ejector mechanism into said steam slot.

14. A surgical scalpel assembly as in claim 1 where said shield is linearly fitted onto said handle by raising said slot of said shield locking mechanism and sliding of said shield onto said distal end of said handle and said shield is removed the raising said slot of said shield locking mechanism and sliding said shield over said distal end of said handle, whereby action of raising said slot of said shield locking mechanism being opposite of normal operating action to eliminate accidental disengagement of shield from handle.

* * * * *